United States Patent
Chun et al.

(10) Patent No.: US 10,582,903 B2
(45) Date of Patent: Mar. 10, 2020

(54) INTRAORAL SENSOR

(71) Applicants: Rayence Co., Ltd., Gyeonggi-do (KR); VATECH EWOO Holdings Co., Ltd., Gyeonggi-do (KR)

(72) Inventors: Jin Pyo Chun, Gyeonggi-do (KR); Tae Woo Kim, Gyeonggi-do (KR); Hyung Keun Lim, Gyeonggi-do (KR); Sung Kyn Heo, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 301 days.

(21) Appl. No.: 15/532,954

(22) PCT Filed: Dec. 2, 2015

(86) PCT No.: PCT/KR2015/013065
§ 371 (c)(1),
(2) Date: Jun. 2, 2017

(87) PCT Pub. No.: WO2016/089113
PCT Pub. Date: Jun. 9, 2016

(65) Prior Publication Data
US 2018/0160991 A1   Jun. 14, 2018

(30) Foreign Application Priority Data
Dec. 2, 2014   (KR) .................. 10-2014-0170678

(51) Int. Cl.
*A61B 6/14*   (2006.01)
*A61B 6/00*   (2006.01)
(Continued)

(52) U.S. Cl.
CPC .............. *A61B 6/145* (2013.01); *A61B 6/425* (2013.01); *A61B 6/56* (2013.01); *G01N 23/04* (2013.01); *H04N 5/32* (2013.01)

(58) Field of Classification Search
CPC .. A61B 6/00; A61B 6/14; A61B 6/145; A61B 6/425; A61B 6/56; A61B 6/4283;
(Continued)

(56) References Cited

U.S. PATENT DOCUMENTS 5,514,873 A      5/1996  Schulze-Ganzlin et al.
7,210,847 B2 *   5/2007  Hack .................... A61B 6/145
                                              206/455
(Continued)

FOREIGN PATENT DOCUMENTS

CN   101808583 A   8/2010
CN   106793995 A   5/2017
(Continued)

OTHER PUBLICATIONS

Korean Intellectual Property Office, International Search Report of International Application No. PCT/KR2015/013065, dated Aug. 30, 2016.
(Continued)

Primary Examiner — Jurie Yun
(74) Attorney, Agent, or Firm — IP Legal Services, LLC

(57) ABSTRACT

The present invention provides an intraoral sensor that includes: a sensor panel generating an electrical signal by detecting X-rays; an elasticity-adjusting member disposed behind the sensor panel and limiting elasticity of the sensor panel; a wireless communication circuit disposed behind the elasticity-adjusting panel, transmitting the electrical signal generated by the sensor panel to an external console wirelessly, and receiving the electrical signal from the console
(Continued)

wirelessly; and a battery module disposed behind the elasticity-adjusting member and supplying power.

6 Claims, 3 Drawing Sheets

(51) Int. Cl.
*G01N 23/04* (2018.01)
*H04N 5/32* (2006.01)

(58) Field of Classification Search
CPC .......... A61B 6/44; A61B 6/4411; H04N 5/32; G01N 23/04; G03B 42/04; G03B 42/042
USPC ........................................ 378/168, 184, 191
See application file for complete search history.

(56) References Cited

U.S. PATENT DOCUMENTS

| | | |
|---|---|---|
| 2004/0065836 A1 | 4/2004 | Schick et al. |
| 2004/0065837 A1 | 4/2004 | Schick et al. |
| 2004/0066898 A1 | 4/2004 | Schick et al. |
| 2006/0067462 A1 | 3/2006 | Hack |
| 2006/0193436 A1 | 8/2006 | Schick et al. |
| 2006/0262461 A1 | 11/2006 | Wood |
| 2007/0053498 A1 | 3/2007 | Mandelkern et al. |
| 2009/0034687 A1 | 2/2009 | Ayraud |
| 2010/0220839 A1 | 9/2010 | Takagi et al. |
| 2012/0076266 A1 | 3/2012 | Kim et al. |
| 2013/0334427 A1 | 12/2013 | Kaneko et al. |
| 2016/0038104 A1 | 2/2016 | Heo et al. |
| 2017/0224294 A1 | 8/2017 | Heo et al. |
| 2017/0224295 A1 | 8/2017 | Heo |
| 2017/0224296 A1 | 8/2017 | Heo |

FOREIGN PATENT DOCUMENTS

| | | |
|---|---|---|
| EP | 3178398 A1 | 6/2017 |
| EP | 3178399 A1 | 6/2017 |
| EP | 3178400 A1 | 6/2017 |
| JP | 2006-521130 A | 9/2006 |
| JP | 2009-080032 A | 4/2009 |
| JP | 2011-120925 A | 6/2011 |
| KR | 10-2012-0028852 A | 3/2012 |
| KR | 10-2014-0053713 A | 5/2014 |
| WO | 2006/103126 A1 | 10/2006 |
| WO | 2017/069514 A1 | 4/2017 |

OTHER PUBLICATIONS

Korean Intellectual Property Office, Written Opinion of International Application No. PCT/KR2015/013065, dated Aug. 30, 2016.
European Patent Office, Extended European Search Report of corresponding EP Patent Application No. 15866190.0, dated Jul. 27, 2018.
The State Intellectual Property Office of People's Republic of China, Office Action of corresponding CN Patent Application No. 201580074321.9, dated Dec. 31, 2019.

* cited by examiner

INTRAORAL SENSOR

CROSS REFERENCE TO RELATED APPLICATIONS

This application is a National Stage Patent Application of PCT International Patent Application No. PCT/KR2015/013065 (filed on Dec. 2, 2015) under 35 U.S.C. § 371, which claims priority to Korean Patent Application No. 10-2014-0170678 (filed on Dec. 2, 2014), the teachings of which are incorporated herein in their entireties by reference.

TECHNICAL FIELD

The present invention relates to an intraoral sensor and, more particularly, an intraoral sensor that can perform wireless communication.

BACKGROUND ART

A type of using film was used in medical or industrial X-ray scanning.

However, the type of using film was inefficient in terms of cost and time due to problems with developing and keeping the film. In order to solve this problem, digital image sensors are extensively used now.

Such digital sensors are used widely as intraoral sensors. Modern intraoral sensors are generally connected with a cable to perform data communication and receive power through the cable.

However, intraoral sensors that are connected by cables cause various inconveniences in use.

In X-ray scanning using such an intraoral sensor, a cable is put in a patient's mouth and is in contact with teeth or portions around the mouth of a patient, so the patient feels considerable discomfort and stress.

Further, poor X-ray scanning may be caused due to entanglement of a cable in using or keeping.

Further, cables are several meters long, so it is not easy to keep or install them.

As described above, intraoral sensors using cables have many problems in terms of convenience of use.

DISCLOSURE

Technical Problem

An object of the present invention is to provide a solution that can improve convenience of using an intraoral sensor.

Technical Solution

In order to achieve the object, the present invention provides an intraoral sensor that includes: a sensor panel generating an electrical signal by detecting X-rays; an elasticity-adjusting member disposed behind the sensor panel and limiting elasticity of the sensor panel; a wireless communication circuit disposed behind the elasticity-adjusting panel, transmitting the electrical signal generated by the sensor panel to an external console wirelessly, and receiving the electrical signal from the console wirelessly; and a battery module disposed behind the elasticity-adjusting member and supplying power.

The intraoral sensor may include a driving circuit module being a printed circuit board having the wireless communication circuit, and disposed behind the elasticity-adjusting member, in which the battery module may be formed in a thin film shape and disposed behind the driving circuit module.

The intraoral sensor may include: a first case protecting a front portion of the sensor panel; a grip holder having a body and a contact portion disposed at rear part of the body and being in contact with a rear portion of the battery module; a second case covering the first case and the contact portion; and a housing covering the second case.

The wireless communication module may be disposed inside the grip holder.

The sensor panel may include a substrate and photoelectric transformation elements on the substrate, and the thickness of the substrate may be 30 um~70 um.

The elasticity-adjusting member may have a first direction elasticity smaller than a second direction elasticity, and the first direction may be a direction of a longer axis of the intraoral sensor and the second direction may be a direction of a shorter axis of the intraoral sensor.

An elasticity ratio of the first direction elasticity and the second direction elasticity may be 1:1.5 to 1:6.

According to another aspect, the present invention provides an intraoral sensor that includes: a sensor panel generating the electrical signal by detecting X-rays; a wireless communication circuit providing wireless communication between the sensor panel and the outside; a thin film-shaped battery module; and a housing covering the sensor panel, the wireless communication circuit, and the battery module, in which the intraoral sensor is bendable in accordance with a positional relationship of a intraoral structure.

According to the present invention, a wireless communication module and a battery module are disposed in an intraoral sensor. Accordingly, the intraoral sensor can be individually used without being connected to a separate cable for data communication and power supply.

Therefore, the problem of patient discomfort, use and storage due to the use of the conventional wired cable is solved, then it is possible to maximize convenience of the intraoral sensor in use.

Further, the intraoral sensor can be given a bending property within a predetermined range. Therefore, it is possible to minimize image distortion and alleviate discomfort that a patient feels.

MODE FOR INVENTION

Hereinafter, embodiments of the present invention will be described in detail with reference to the accompanying drawings.

An intraoral sensor is configured in a wireless type in an embodiment of the present invention, so it is possible to solve the problem of discomfort when using wired intraoral sensors of the related art. Further, an intraoral sensor according to an embodiment of the present invention is given flexibility, so it is possible to reduce image distortion and discomfort to a patient. The flexibility means not only a flexible property, but bendable property.

An intraoral sensor according to an embodiment of the present invention having these characteristics is described in detail hereafter.

Figure 1:
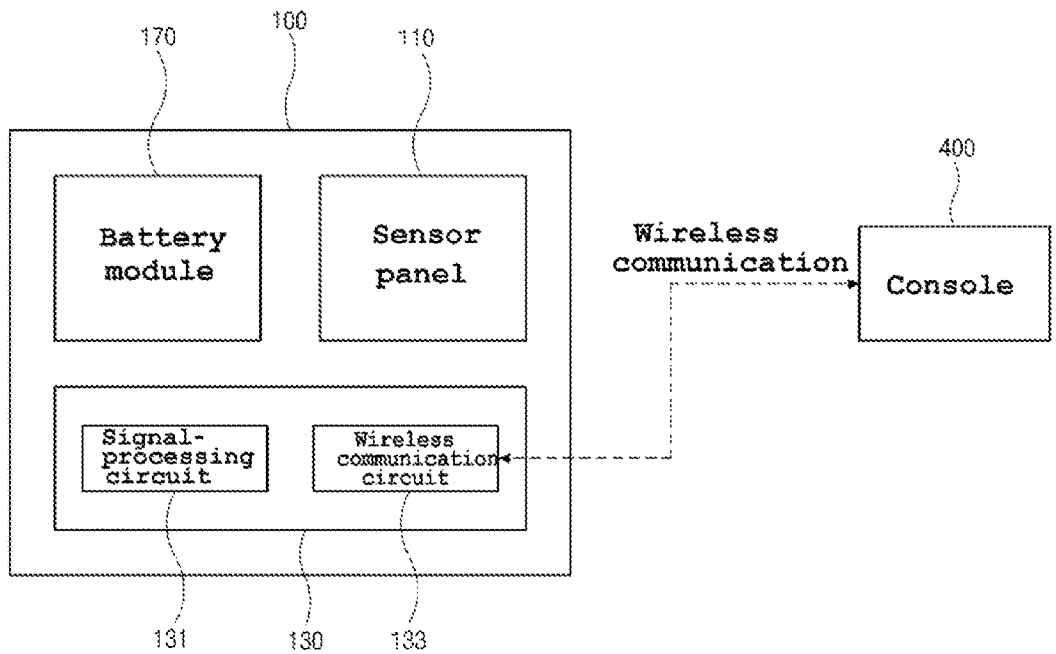
FIG. 1 is a block diagram schematically showing the configuration of an intraoral sensor according to an embodiment of the present invention.

FIG. 1 is a block diagram schematically showing the configuration of an intraoral sensor according to an embodiment of the present invention. A mechanical configuration is not shown in FIG. 1 for the convenience of description.

Referring to FIG. 1, an intraoral sensor 100 according to an embodiment of the present invention may include a sensor panel 110, an driving circuit module 130, and a battery module 170.

The driving circuit module 130 may include a signal-processing circuit 131 that processes electrical signals input/output to/from the sensor panel 110 and a wireless communication circuit 133 that performs wireless communication with a console 400 that is an external system.

As described above, since the intraoral sensor 100 includes the signal-processing circuit 131 and the wireless communication circuit 133 in an embodiment of the present invention, the intraoral sensor 100 can be configured in a wireless type.

Meanwhile, as the intraoral sensor 100 is configured in a wireless type, it is not possible to receive a separate driving power from the outside, so the intraoral sensor 100 provided with the battery module 170 as a power source. The battery module 170 may be formed in a thin film type, but is not limited thereto.

Figure 2:
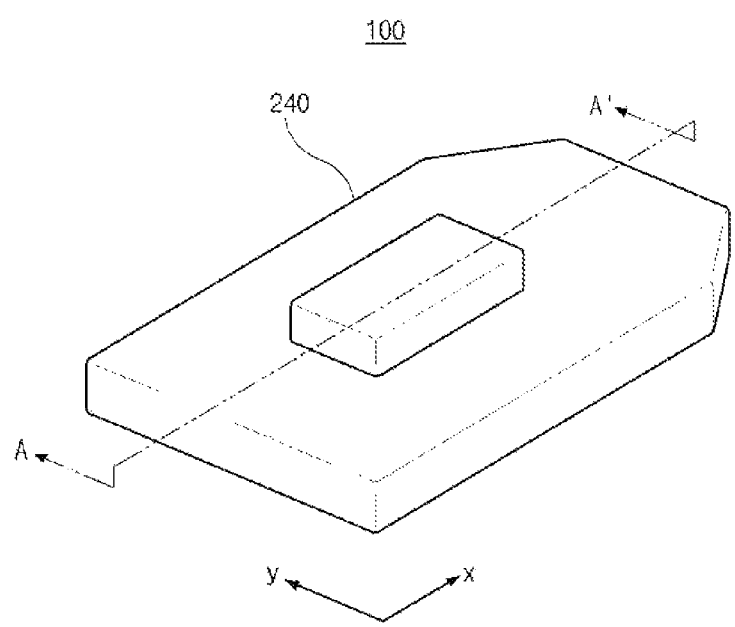
FIG. 2 is a perspective view schematically showing the intraoral sensor according to an embodiment of the present invention.
Figure 4:
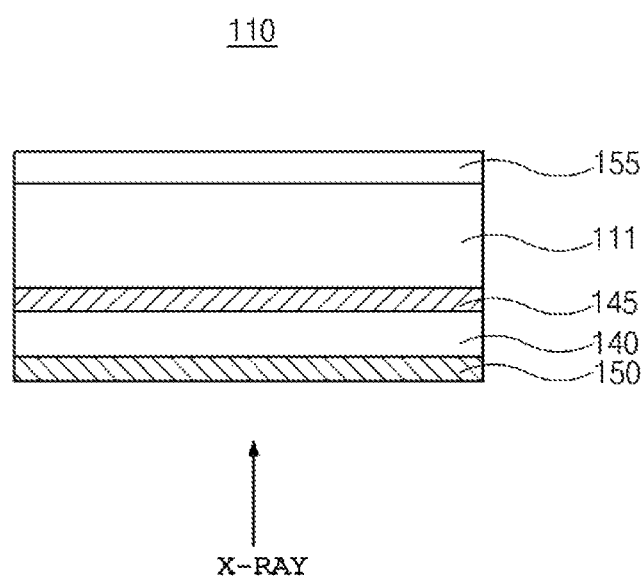
FIG. 4 is a cross-sectional view schematically showing a sensor panel according to an embodiment of the present invention.
Figure 5:
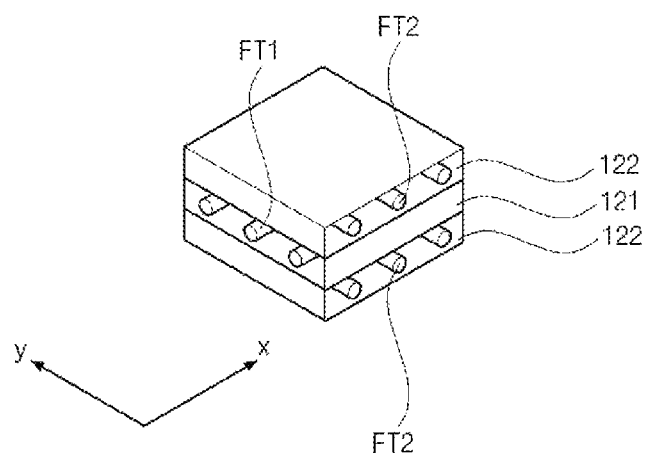
FIG. 5 is a view enlarging a portion of an elasticity-adjusting member according to an embodiment of the present invention.

Hereinafter, the structure of the intraoral sensor 100 having the wireless communication configuration, as described above, is described in detail hereafter. FIG. 2 is a perspective view schematically showing the intraoral sensor according to an embodiment of the present invention, FIG. 3 is a cross-sectional view taken along line A-A' of FIG. 2, FIG. 4 is a cross-sectional view schematically showing a sensor panel according to an embodiment of the present invention, and FIG. 5 is a view enlarging a portion of an elasticity-adjusting member according to an embodiment of the present invention.

Figure 3:
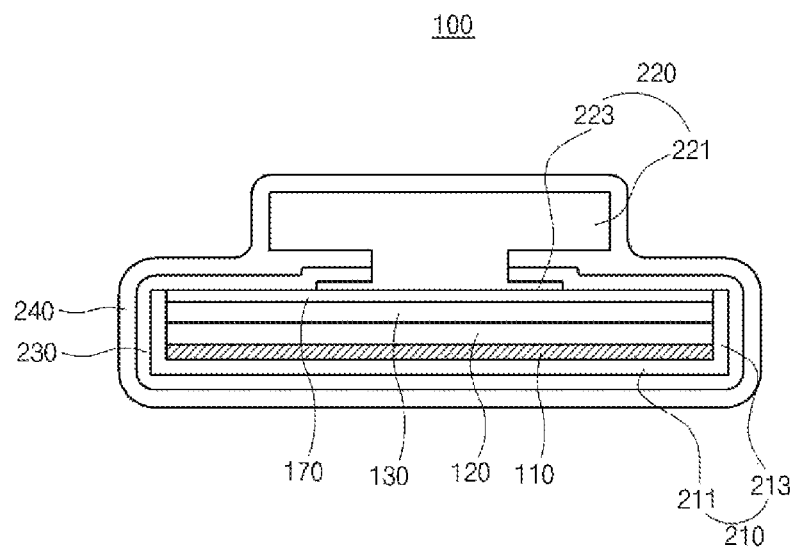
FIG. 3 is a cross-sectional view taken along line A-A' of FIG. 2.

Referring to FIGS. 2 and 3 showing the configuration of the intraoral sensor 100, the intraoral sensor 100 may include a sensor panel 110 arranged in the X-axial direction, an elasticity-adjusting member 120, the driving circuit module 130, and the thin film-shaped battery module 170.

The thin film-shaped battery module 170 may be disposed between the elasticity-adjusting member 120 and the driving circuit module 130.

For the convenience of description, the components inside the intraoral sensor 100 are, in combination, referred to as a core module 101.

The intraoral sensor 100 may include, as mechanical components for protecting and supporting the core module 101, a first case 210 protecting the front side of the core module 101, a grip holder 220 supporting the rear side of the core module 101, a second case 230 coupling the first case 210 and the grip holder 220, and a housing 240 covering the second case 230.

A plurality of pixels is arranged in rows and columns in a matrix shape in an effective area for obtaining images, that is, an active area on the sensor panel 110. A photoelectric transformation element such as a photodiode and a switching element are disposed in each of the pixels, and the elements convert incident light into an electrical signal and transmit the electrical signal. The switching element may be a CMOS transistor or a TFT.

Though not described in detail, pads for outputting electrical signals are disposed on a side of the sensor panel 110.

In the implementation of the bendable property of the intraoral sensor 100, the sensor panel 110 is also configured to have the bendable property. To this end, assuming that the sensor panel 110 includes a brittle substrate such as a semiconductor, ceramic, or glass, it is preferable that the thickness of the substrate may be 100 um or less, for example, 30 um~70 um. By forming the substrate of the sensor panel 110 with such a thickness, the bending strength of the sensor panel 110 can be optimized.

In order to making the substrate having the thickness, for example, a way of removing the rear side of a substrate at a predetermined thickness may be used. That is, it is possible to make the substrate thin, as described above, by performing a process such as mechanical grinding, chemical grinding, or plasma etching on the rear side opposite to the side with the photoelectric transformation element.

The sensor panel 110 may be a direct-converting type sensor panel that directly converts an incident X-ray into an electrical signal or an indirect-converting type sensor panel that converts an incident X-ray into visible light and then converts it into an electrical signal.

When the sensor panel 110 is an indirect-converting type, as shown in FIG. 4, a scintillator layer 140 for converting an X-ray into visible light may be disposed on a side of the panel 111 of the sensor panel 110, that is, on the photoelectric transformation element.

Although the scintillator layer 140 is disposed on the side that receives the X-rays in the sensor panel 110 in FIG. 4, the scintillator layer 140 may be disposed on the opposite side to the side that receives the X-rays, as another example.

The scintillator layer 140 may be attached to the substrate 111, for example, by an adhesive 145. A radiation-transmissive protective film 150 for protecting the scintillator layer 140 may be disposed on the scintillator layer 140. The adhesive 145 may be a soft adhesive having high light transmittance, for example, an OCA (Optically Clear Adhesive) film and the protective film 150 may be resin film having high radiation transmittance and humidity interception ability. For reference, the adhesive may have a thickness of 10~50 um, preferably, 15~40 um under the assumption that it is an OCA film, to have a function of reducing brittleness of the substrate.

The fluorescent substance of the scintillator layer 140 may be, for example, a fluorescent substance containing CsI or a fluorescent substance containing Gadox (Gd2O2: Tb).

When the intraoral sensor 110 according to an embodiment of the present invention is bendable, a fluorescent substance containing Gadox is preferable rather than a fluorescent substance containing CsI having a columnar crystal structure. The Gadox fluorescent substance has a particulate structure, so possibility of damage of the substance is very low, even if the intraoral sensor 110 bends, so a defect is not generated. Further, the scintillator layer 140 using Gadox is easy to manufacture.

For reference, the scintillator layer 140 using Gadox may be 250~500 um, preferably, 300~450 um thick to obtain a sufficient amount of light.

A flexible layer 155 may be formed on the side opposite to the side, where the scintillator layer 140 is formed, of the substrate 111 and may be made of resin having flexibility such as polyimide (PI). The flexible layer 155 may be thick enough to prevent damage by reducing the brittleness of the substrate 111 with respect to bending of an intraoral sensor, for example, may have a thickness of 50~150 um.

The driving circuit module 130 may be formed in a plate type using a PCB (Printed Circuit Board) and may be disposed behind the sensor panel 110. The driving circuit module 130 is electrically connected to a side of the sensor panel 110, wirelessly transmits electrical signals generated from the sensor panel 110 to the external console 400, and receives signals from the console 400.

The signals are transmitted wirelessly, and to this end, the driving circuit module 130 may include the wireless communication circuit 133.

The wireless communication circuit 133 includes a transmitter and a receiver, so it can transmit/receive signals in a wireless type using them.

As another example, the wireless communication circuit 133 may be disposed outside the driving circuit module 130, and for example, the wireless communication circuit 133 may be formed in a small size and disposed in the grip holder 220. In this case, the driving circuit module 130 and the wireless communication circuit 133 may be electrically connected to each other through a transmission wire.

Further, the driving circuit module 130 may be formed in a small size and disposed in the grip holder 220, and accordingly, the wireless communication circuit 133 of the driving circuit module 130 may be disposed in the grip holder 220.

By placing the driving circuit module 130 or the wireless communication circuit 133 in the grip holder 220, as described above, it is possible to further reduce the thickness or the size of the intraoral sensor 100.

On the other hand, for the driving circuit module 130 formed in a substrate type, a flexible substrate made of a flexible material may be used for implementing the bendable property for the intraoral sensor 100.

In order to implementing the bendable property for the intraoral sensor 100, the thickness of the driving circuit module 130 may be 150~350 um, but is not limited thereto, and it has only to have elasticity less than the sensor panel 110.

For example, the elasticity-adjusting member 120 is disposed between the sensor panel 110 and the driving circuit module 130 and may be formed to cover the entire rear side of the sensor panel 110.

The elasticity-adjusting member 120 may be made of an elastic material having elasticity larger than the sensor panel 110 or the driving circuit module 130.

Accordingly, the elasticity-adjusting member 120 can adjust the degree of bending of the sensor panel 110 and the driving circuit module 130, that is, the elasticity of the sensor panel 110 and the driving circuit module 130 under the degree of bending of the elasticity-adjusting member 120, that is, over the elasticity of the elasticity-adjusting member 120.

Accordingly, the elasticity-adjusting member 120 provides a bendable property and a restoring force to the intraoral sensor 100 while changing the degree of bending in accordance with the magnitude of external force within the elasticity limit of the elasticity-adjusting member 120, and protects the intraoral sensor 100 by reducing the brittleness of the sensor panel 110 with respect to bending of the intraoral sensor 100.

That is, the elasticity of the components may depend on the size or the thickness thereof, but assuming that the elasticity of the sensor panel 110 is first elasticity and the elasticity of the driving circuit module 130 is second elasticity, the first elasticity is generally equal to or more than the second elasticity. Further, the elasticity-adjusting member 120 is made of a material having third elasticity over the first elasticity, so it adjusts the elasticity of the sensor panel 110 and the printed circuit board over the third elasticity such that the intraoral sensor 100 is bendable within the elasticity limit of the elasticity-adjusting member 120 and the intraoral sensor 100 bends within the elasticity limit of the elasticity-adjusting member 120 and then return to the initial shape after external force is removed.

To this end, the elasticity-adjusting member 120 may be made of a resin material, particularly, a composite composed of two or more resin materials, and compounded resin including a reinforcement and resin may be used.

Further, the elasticity-adjusting member 120 may be configured such that the bending property in a first direction and the bending property in a second direction perpendicular to the first direction are different in a plane.

Accordingly, if the intraoral sensor 100 is formed in rectangular shape that is longer in the x-axial direction than in the y-axial direction in a plane, the elasticity-adjusting member 120 may be formed such that the bending property in the x-axial direction that is the direction of the longer axis is larger than the bending property in the y-axial direction that is the direction of the shorter axis. Even if the intraoral sensor 100 is formed substantially in a square, the bending properties can be different in the x-axial and y-axial directions.

By these bending abilities, the intraoral sensor 10 is more bendable in the direction of the longer axis than the direction of the shorter axis, so it is possible to effectively alleviate discomfort of a patient when scanning the inside of the mouth using the intraoral sensor 100.

In this regard, in scanning of the inside of a mouth, the corners of the intraoral sensor 100 cause a patient discomfort, and particularly, the ends in the direction of the longer axis further make the patient feel inconvenient. Accordingly, by giving the bending property, particularly, the bending property larger in the direction of the longer axis to the bending property of the intraoral sensor 100, it is possible to considerably alleviate the discomfort that a patient feels.

Further, since the elasticity-adjusting member 120 has the bending property larger in the x-axial direction that is the direction of the longer axis than in the y-axial direction that is the direction of the shorter axis, distortion stress is distributed in the x- and y-axial directions and most of the distortion stress is converted into stress in the x-axial direction, so it is possible to prevent the sensor panel 110, particularly, the substrate 111 being damaged.

As described above, the elasticity-adjusting member 120 having different bending properties in accordance of directions in a plane may be made of a composite composed of resin materials, for example, FRP (Fiber Reinforced Polymer) including a fiber reinforcement. The FRP is obtained by adding inorganic fiber such as glass fiber, carbon fiber, and boron fiber or organic fiber such as aramid fiber, polyester fiber, and Keblar fiber, as a fiber reinforcement, to thermosetting resin such as unsaturated polyester, epoxy, phenol, and polyimide or thermoplastic resin such as polyamide, polycarbonate, ABS, PBT, PP, and SAN.

The case when the elasticity-adjusting member 120 has a bending property larger in the x-axial direction that is the direction of a longer axis than in the y-axial direction that is the direction of a shorter axis is described with reference to FIG. 5.

Referring to FIG. 5, a first yarn layer 121 on which a first yarn FT1 is arranged in a first direction, that is, the x-axial direction, and a second yarn layer 122 on which a second yarn FT2 is arranged in a second direction that is, the y-axial direction is alternately arranged along the thickness direction in a state of being impregnated in a resin base material. The first and second yarns FT1 and FT2 may be formed by assembling and knitting the above-mentioned fibers in one direction.

In particular, the number of the first yarn layer 121 having the first yarn FT1 arranged in the x-axial direction, that is, the direction of the longer axis is larger than the number of the second yarn layer 122 having the second yarn FT2 arranged in the y-axial direction, that is, the direction of the shorter axis, and for the sake of convenience of description, one first yarn layer 121 and two second yarn layers 122 are shown in FIG. 5. Further, the first and second yarns FT1 and FT2 are carbon materials and CFRP may be used for the elasticity-adjusting member 120 according to an embodiment of the present invention.

As described above, since the number of the first yarn layers 121 in the direction of the longer axis is smaller than the number of the second yarn layers 122 in the direction of the shorter axis, lower elasticity, that is, a larger bending property is shown in the direction of the longer axis, and higher elasticity, that is, a smaller bending property is shown in the direction of the shorter axis.

The ratio of the elasticity in the direction of the longer axis and the elasticity in the direction of the shorter axis may be about 1:1.5~1:6. Further, the thickness of the elasticity-adjusting member 120 may be about 200~400 um. When the elasticity-adjusting member 120 has a thickness of 300 um, the elasticity-adjusting member 120 may be formed such that the elasticity in the direction of the longer axis shows bending strength of 1000~30000 MPa and the elasticity in the direction of the shorter axis shows bending strength of 1500~180000 Mpa, in which the strength may be applied to thicknesses of 200~400 um.

By stacking different numbers of yarn layers 121 and 122 of which the yarns are arranged across each other, as described above, the elasticity-adjusting member 120 having a bending property larger in the direction of the longer axis than in the direction of the shorter axis can be achieved.

Another example of the elasticity-adjusting member 120 according to an embodiment of the present invention is described with reference to FIG. 6.

Figure 6:
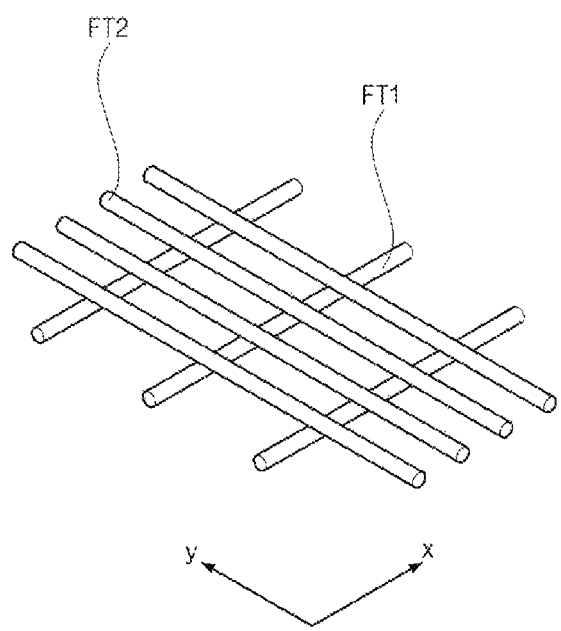
FIG. 6 is a view showing another example of the elasticity-adjusting member according to an embodiment of the present invention.

Referring to FIG. 6, first yarns FT1 arranged in a first direction, i.e., the x-axial direction and second yarns FT2 arranged in a second direction, i.e., the y-axial direction are in a state of impregnated in a resin base material, and particularly, the first yarns FT1 arranged in the first direction, that is, the x-axial direction are smaller in density (that is, gap) than the second yarns FT2 arranged in the second direction, that is, the y-axial direction. It is preferable that the first and second yarns FT1 and FT2 are made of a carbon material and CFRP may be used.

As described above, since the density of the first yarn layers 121 arranged in the direction of the longer axis is smaller than the density of the second yarn layers 122 arranged in the direction of the shorter axis, lower elasticity, that is, a larger bending property is shown in the direction of the longer axis, and higher elasticity, that is, a smaller bending property is shown in the direction of the shorter axis.

Similar to the previous example, the ratio of the elasticity in the direction of the longer axis and the elasticity in the direction of the shorter axis may be about 1:1.5~1:6. Further, the elasticity-adjusting member 120 may be about 200~400 um thick. When the elasticity-adjusting member 120 has a thickness of 300 um, the elasticity-adjusting member 120 may be formed such that the elasticity in the direction of the longer axis shows bending strength of 1000~30000 MPa and the elasticity in the direction of the shorter axis shows bending strength of 1500~180000 Mpa, in which the strength may be applied to thicknesses of 200~400 um.

It is possible to realize the elasticity-adjusting member 120 having a higher bending property in the major axis direction than the minor axis direction by varying the densities of the first and second yarns FT1 and FT2 crossing each other in the above described manner.

Referring to FIGS. 2 and 3 again, the thin film-shaped battery module 170 is disposed in the intraoral sensor 100.

As described above, since the intraoral sensor 100 according to an embodiment of the present invention is configured to transmit signals wirelessly, the battery module 170 that is a separate power source is disposed in the intraoral sensor 100 and supplies power to the driving circuit module 130 and the sensor panel 110.

The battery module 170 may be formed in a thin film type in consideration of the thickness of the intraoral sensor 100. Accordingly, even though the battery module 170 is disposed in the intraoral sensor 100, the thickness of the intraoral sensor 100 is not substantially largely increased Further, when the intraoral sensor 100 is bendable, the battery module 170 can also be made of a flexible material.

On the other hand, even though the intraoral sensor 100 is bendable, a non-flexible battery module 170 having substantially no bending property may be used. In this case, the battery module 170 may be positioned corresponding to the center portion supported by the grip holder 220 as a center portion having a relatively lower bendable property in the intraoral sensor 100. Accordingly, it is possible to prevent the battery module 170 from being damaged due to bending of the intraoral sensor 100.

The battery module 170 can be charged in a wired type or a wireless type. When the battery module 170 is designed to be charged in a wired type, a connector for connecting a charging cable is provided to the intraoral sensor 100, and for example, a charging connector may be provided at the grip holder 220.

In the components described above, the sensor panel 110, the elasticity-adjusting member 120, the driving circuit module 130, and the battery module 140 may be combined into the core module 101. In order to combine these components, adjacent components may be combined by an adhesive, and the adhesive may be OCA having high ductility, but is not limited thereto.

Referring to FIGS. 2 and 3 again, the first case 210 that is a mechanical component, also called a window cover, of the intraoral sensor 100 is positioned ahead of the sensor panel 110. The first case 210 accommodates the core module 101 including the sensor panel 110 and may have the shape of a box with the rear side opened.

That is, the first case 210 may have a base 211 being in contact with the front side of the sensor panel 110 and facing an X-ray source and side walls 213 perpendicularly bended rearward from the edges of the base 211.

The grip holder 2220 is located on the rear side of the sensor panel 110. During the intraoral X-ray imaging, the grip holder 220 is contacted or connected to the user's fingers to support the intraoral sensor 100.

The grip holder 220 may include a body 221 and a plate-shaped contact portion 223 disposed under the body 221, connected to the body 221, and extending outward. The grip holder 220 may be formed in a single unit by molding, but is not limited thereto.

The contact portion 223 is positioned corresponding to the center portion of the sensor panel 110. The front surface of the contact portion 223 is the rear side of the core module 101, and for example, supports the rear portion of the core module 101 in contact with the rear side of the battery module 170. Accordingly, the degree of bending at the center portion of the core module 101 supported by the contact portion 223 can be limited by the contact portion 223.

That is, the center portion of the intraoral sensor 100 corresponding to the contact portion 223 bends less than the other portion surrounding the center, so it is possible to alleviate discomfort of a patient and minimize image distortion.

In the components described above, the core module 101, the first case 210 positioned ahead of the core module, and the grip holder 220 positioned behind the core module are assembled in a module. The second case 230 may be used for more strongly combining them. The second case 230 may be a molded case.

The second case 230 may cover the front side and sides of the first case 210, the rear side of the core module 101, and the rear side of the contact portion 223.

The second case 230, may be, made of a resin material that is cured by UV, but is not limited thereto. In particular, in consideration of the bending property within a limited range, the second case 230 may be made of a material having a Shore hardness of about D 10~20, but is not limited thereto.

The intraoral sensor 100 can be covered with the housing 240 by molding the intraoral sensor 100 having the second case 230. In this configuration, a portion of the grip holder 220 may not be covered with the housing 240.

The housing 240 may be made of a soft material, for example, silicon or urethane. In particular, the housing 240 may be made of a soft material having a Shore hardness of about A 30~50, but is not limited thereto.

Using the housing 240 made of a soft material can considerably reduce pain that a patient feels during oral scanning.

As described above, according to an embodiment of the present invention, a wireless communication circuit and a battery module are disposed in the intraoral sensor. Accordingly, the intraoral sensor can be individually used without being connected to a separate cable for data communication and power supply.

Therefore, the discomfort that a patient feels and the problems in using and keeping due to a cable are removed, so it is possible to maximize convenience of the intraoral sensor in use.

Further, the intraoral sensor can be given a bending property within a predetermined range. Therefore, the intraoral sensor is bendable in accordance with the positional relationship of the intraoral structure, so it is possible to minimize image distortion and reduce user discomfort.

The invention claimed is:

1. An intraoral sensor comprising:
a bendable sensor panel generating an electrical signal by detecting X-rays;
an elasticity-adjusting member disposed behind the bendable sensor panel and limiting elasticity of the bendable sensor panel;
a wireless communication circuit disposed behind the elasticity-adjusting member, transmitting the electrical signal generated by the bendable sensor panel to an external console wirelessly, and receiving an electrical signal from the console wirelessly;
a battery module disposed behind the elasticity-adjusting member and supplying power; and
a driving circuit module including a printed circuit board having the wireless communication circuit and disposed behind the elasticity-adjusting member, wherein:
the battery module is formed in a thin film shape and disposed behind the driving circuit module,
the elasticity-adjusting member has a first direction elasticity smaller than a second direction elasticity, and
the first direction is a direction of a longer axis of the intraoral sensor and the second direction is a direction of a shorter axis of the intraoral sensor.

2. The intraoral sensor of claim 1, further comprising:
a first case protecting a front portion of the sensor panel;
a grip holder having a body and a contact portion disposed under the body and being in contact with a rear portion of the battery module;
a second case covering the first case and the contact portion; and
a housing covering the second case.

3. The intraoral sensor of claim 2, wherein the wireless communication circuit is disposed inside the grip holder.

4. The intraoral sensor of claim 1, wherein the sensor panel includes a substrate and a photoelectric transformation element on the substrate, and
a thickness of the substrate is 30 um~70 um.

5. The intraoral sensor of claim 1, wherein an elasticity ratio of the first direction elasticity and the second direction elasticity is 1:1.5 to 1:6.

6. The intraoral sensor of claim 1, further comprising:
a grip holder disposed at a rear side of the sensor panel and including the wireless communication circuit.

* * * * *